United States Patent
Edelman et al.

(10) Patent No.: US 9,433,631 B2
(45) Date of Patent: *Sep. 6, 2016

(54) 4-PREGENEN-11β-17-21-TRIOL-3,20-DIONE DERIVATIVES

(71) Applicant: Allergan, Inc., Irvine, CA (US)

(72) Inventors: Jeffrey L. Edelman, Irvine, CA (US); Alissar Nehme, Mission Viejo, CA (US); Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/533,847

(22) Filed: Nov. 5, 2014

(65) Prior Publication Data

US 2015/0057258 A1    Feb. 26, 2015

Related U.S. Application Data

(63) Continuation of application No. 13/673,623, filed on Nov. 9, 2012, now Pat. No. 8,906,892.

(60) Provisional application No. 61/558,775, filed on Nov. 11, 2011.

(51) Int. Cl.

| | |
|---|---|
| *A61K 31/58* | (2006.01) |
| *A61K 31/573* | (2006.01) |
| *C07J 7/00* | (2006.01) |
| *C07J 17/00* | (2006.01) |
| *C07J 31/00* | (2006.01) |
| *A61K 31/56* | (2006.01) |
| *A61K 9/00* | (2006.01) |
| *C07J 5/00* | (2006.01) |
| *A61K 31/575* | (2006.01) |

(52) U.S. Cl.
CPC ............. *A61K 31/58* (2013.01); *A61K 9/0048* (2013.01); *A61K 31/56* (2013.01); *A61K 31/573* (2013.01); *C07J 5/0053* (2013.01); *C07J 7/008* (2013.01); *C07J 17/00* (2013.01); *C07J 31/006* (2013.01); *A61K 31/575* (2013.01)

(58) Field of Classification Search
CPC .. A61K 31/58; A61K 31/573; A61K 9/0048; C07J 5/0053; C07J 7/008; C07J 31/006
See application file for complete search history.

(56) References Cited

U.S. PATENT DOCUMENTS

| | | | |
|---|---|---|---|
| 3,484,436 A | 12/1969 | Cross | |
| 3,557,162 A | 1/1971 | Lens | |
| 3,984,544 A | 10/1976 | Casmer | |
| 4,242,334 A | 12/1980 | Stache | |
| 5,362,721 A | 11/1994 | Stache | |
| 8,524,697 B2 | 9/2013 | Anthes et al. | |
| 8,906,892 B2 * | 12/2014 | Edelman | C07J 7/008 514/172 |
| 2005/0245497 A1 | 11/2005 | Penfold et al. | |
| 2011/0182828 A1 | 7/2011 | Anthes et al. | |
| 2013/0123226 A1 | 5/2013 | Edelman et al. | |

FOREIGN PATENT DOCUMENTS

WO    2005-099715    10/2005

OTHER PUBLICATIONS

L.C. Cross et al., Rules for the Nomenclature of Organic Chemistry, Section E: Stereochemistry, International Union of Pure and Applied Chemistry, vol. 45, 1976, pp. 19-30.
P. Heinrich Stahl, Handbook of Pharmaceutical Salts, International Union of Pure and Applied Chemistry, Verlag Helvetica Chemica Acta—Zürich, 2002, 329-345.
Jennifer M. Wilkinson et al., Compound Profiling Using a Panel of Steroid Hormone Receptor Cell-Based Assays, Journal of Biomolecular Screening, 2008, pp. 755-765.
Herbert L. Cantrill, Comparison of In Vitro Potency of Corticosteroids With Ability to Raise Intraocular Pressure, American Journal of Ophthalmology, Jun. 1975, pp. 1012-1017, St. Louis Missouri.
Patent Cooperation Treaty, International Search Report and Written Opinion, PCT Application No. PCT/US2012/064293, Dec. 18, 2012.

* cited by examiner

*Primary Examiner* — Timothy Thomas
(74) *Attorney, Agent, or Firm* — Jonathan Bass

(57) ABSTRACT

The present invention relates to novel 4-pregenen-11β-17-21-triol-3,20-dione derivatives, processes for preparing them, pharmaceutical compositions containing them and their use as pharmaceuticals, as modulators of glucocorticoid or mineralocorticoid receptors. The invention relates specifically to the use of these compounds and their pharmaceutical compositions to treat disorders associated with glucocorticoid or mineralocorticoid receptor modulation.

12 Claims, No Drawings

4-PREGENEN-11β-17-21-TRIOL-3,20-DIONE DERIVATIVES

RELATED APPLICATION

This application is a continuation of U.S. patent application Ser. No. 13/673,623, filed Nov. 9, 2012, and claims the benefit of U.S. Provisional Application Ser. No. 61/558,775, filed Nov. 11, 2011, the disclosures of each of which is hereby incorporated in its entirety herein by reference.

FIELD OF THE INVENTION

The present invention relates to novel 4-pregenen-11β-17-21-triol-3,20-dione derivatives, processes for preparing them, pharmaceutical compositions containing them and their use as pharmaceuticals, as modulators of glucocorticoid or mineralocorticoid receptors. The invention relates specifically to the use of these compounds and their pharmaceutical compositions to treat disorders associated with glucocorticoid or mineralocorticoid receptor modulation.

BACKGROUND OF THE INVENTION

Glucocorticoid (GC) agonists represent a class of anti-inflammatory compounds that are useful in treating multiple ocular conditions including elevated intraocular pressure, glaucoma, uveitis, retinal vein occlusions, macular degeneration, diabetic retinopathy, various forms of macular edema, post-surgical inflammation, inflammatory conditions of the palpebral and bulbar conjunctiva, cornea, and anterior segment of the globe, such as allergic conjunctivitis, ocular rosacea, dry eye, blepharitis, retinal detachment, meibomian gland dysfunction (MGD), superficial punctate keratitis, herpes zoster keratitis, iritis, cyclitis, selected infective conjunctivitis, corneal injury from chemical, radiation, or thermal burns, penetration of foreign bodies, allergy, or combinations thereof.

A potential use limiting and sight-threatening side-effect of traditional GC agonist therapies (e.g. fluocinolone acetonide) is ocular hypertension that is likely generated by an increased resistance of aqueous humor flow through the trabecular meshwork.

The mechanism of GC agonist-induced outflow resistance and subsequent ocular hypertension is not well understood. As such, GC modulation through agonist or antagonist activity of GC receptors that does not result in increased intraocular pressure or other side effects is needed in the art and is described herein.

SUMMARY OF THE INVENTION

The present invention relates to novel 4-pregenen-11β-17-21-triol-3,20-dione derivatives useful in treating one or more ocular conditions. Methods of treating one or more ocular conditions are also disclosed. Ocular conditions treated using compounds and/or formulations described herein include, but are not limited to, elevated intraocular pressure, glaucoma, uveitis, retinal vein occlusions, macular degeneration, diabetic retinopathy, various forms of macular edema, post-surgical inflammation, inflammatory conditions of the palpebral and bulbar conjunctiva, cornea, and anterior segment of the globe, such as allergic conjunctivitis, ocular rosacea, dry eye, blepharitis, retinal detachment, meibomian gland dysfunction (MGD), superficial punctate keratitis, herpes zoster keratitis, iritis, cyclitis, selected infective conjunctivitis, corneal injury from chemical, radiation, or thermal burns, penetration of foreign bodies, allergy, or combinations thereof.

In one aspect, the invention therefore provides a compound of Formula I, its enantiomers, diastereoisomers, hydrates, solvates, crystal forms and individual isomers, tautomers or a pharmaceutically acceptable salt thereof,

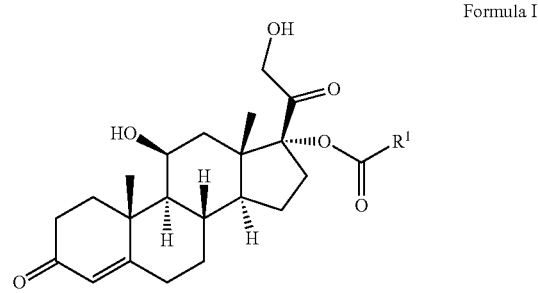

Formula I wherein:

$R^1$ is optionally substituted $C_7$-$C_{11}$ alkyl, optionally substituted $C_2$-$C_8$ alkenyl, optionally substituted $C_2$-$C_8$ alkynyl, optionally substituted $C_4$ or $C_{6-8}$ cycloalkyl, optionally substituted aryl, substituted benzyl, optionally substituted heterocycle, optionally substituted $C_3$-$C_{10}$ cycloalkenyl, optionally substituted $C_5$-$C_{10}$ cyclodiene, optionally substituted $O(C_3$-$C_6)$ alkyl, amino groups, sulfonamide groups, amide groups, except phenyl.

In another embodiment, the invention therefore provides a compound of Formula I, wherein $R^1$ is selected from:

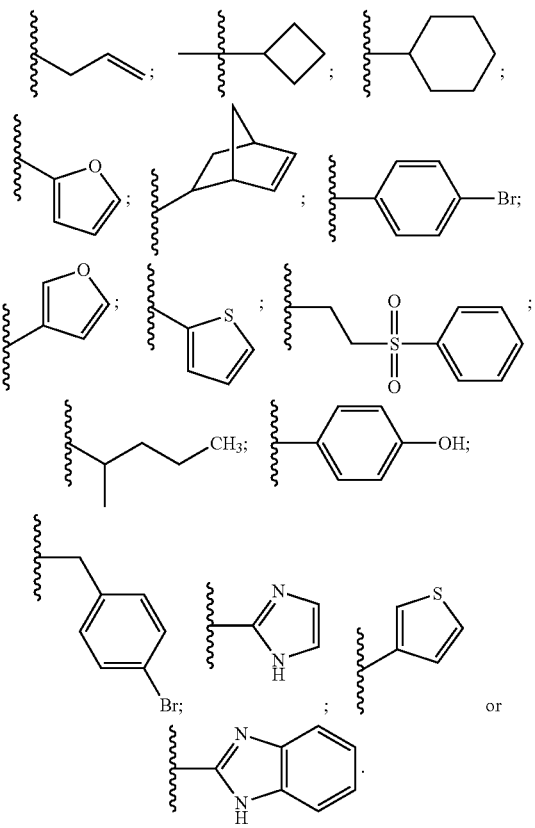

The term "alkyl", as used herein, refers to saturated, monovalent or divalent hydrocarbon moieties having linear or branched moieties or combinations thereof and containing 7 to 11 carbon atoms. One methylene (—$CH_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can be independently substituted by halogen atoms, hydroxyl groups, cycloalkyl groups, amino groups, heterocyclic groups, aryl groups, carboxylic acid groups, ester groups, ketone groups, phosphonic acid groups, sulphonic acid groups, phosphoric acid groups, nitro groups, amide groups, sulfonamide groups.

The term "cycloalkyl", as used herein, refers to a monovalent or divalent group of 4, and 6 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$OC_{1-8}$ alkyl groups, —$SC_{1-8}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "cycloalkenyl", as used herein, refers to a monovalent or divalent group of 3 to 10 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "cyclodiene", as used herein, refers to a monovalent or divalent group of 5 to 10 carbon atoms derived from a saturated cycloalkyl having two double bonds. Cyclodiene groups can be monocyclic or polycyclic. Cyclodiene groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 8 carbon atoms, derived from a saturated alkyl, having at least one double bond. One methylene (—$CH_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-8}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 8 carbon atoms, derived from a saturated alkyl, having at least one triple bond. One methylene (—$CH_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 member ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C═O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carbocyclic acid groups, $C_{1-6}$ alkyl carboxylates (ester) groups, amide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —(CO)$R^x$ wherein $R^x$ can be alkyl, aryl, cycloalkyl, cycloalkenyl, heterocycle as defined above.

The term "amine" as used herein, represents a group of formula "—$NR^xR^y$", wherein $R^x$ and $R^y$ can be the same or independently hydrogen, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—$SO_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—$NO_2$".

The term "cyano" as used herein, represents a group of formula "—CN".

The term "amide" as used herein, represents a group of formula "—C(O)$NR^xR^y$," wherein $R^x$ and $R^y$ can be the same or independently hydrogen, alkyl, aryl, cycloalkyl, cycloalkenyl, heterocycle as defined above.

The term "ester" as used herein, represents a group of formula "—C(O)O$R^x$," wherein $R^x$ is alkyl, aryl, cycloalkyl, cycloalkenyl, heterocycle as defined above.

The term "sulfonamide" as used herein, represents a group of formula "—S(O)$_2$$NR^xR^y$" wherein $R^x$ and $R^y$ can be the same or independently hydrogen, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Compounds of the invention are:

(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl (4-bromophenyl)acetate;

(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl 3-(phenylsulfonyl)propanoate;

(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl 2-furoate.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, such as for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically. Compounds according to the present invention may exist in different polymorphic forms. Although not explicitly indicated in the above formula, such forms are intended to be included within the scope of the present invention.

The compounds described herein are useful in treating a variety of ocular conditions including, but not limited to elevated intraocular pressure, glaucoma, uveitis, retinal vein occlusions, macular degeneration, diabetic retinopathy, various forms of macular edema, post-surgical inflammation, inflammatory conditions of the palpebral and bulbar conjunctiva, cornea, and anterior segment of the globe, such as allergic conjunctivitis, ocular rosacea, dry eye, blepharitis, retinal detachment, meibomian gland dysfunction (MGD), superficial punctate keratitis, herpes zoster keratitis, iritis, cyclitis, selected infective conjunctivitis, corneal injury from chemical, radiation, or thermal burns, penetration of foreign bodies, allergy, or combinations thereof.

In still another embodiment of the invention, there are provided methods for treating disorders associated with modulation of the glucocorticoid receptors (GR) and/or the mineralocorticoid receptors (MR). receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

In another embodiment, there are provided pharmaceutical compositions including at least one compound of the invention in a pharmaceutically acceptable carrier.

The compounds described herein may be administered at pharmaceutically effective dosages. Such dosages are normally the minimum dose necessary to achieve the desired therapeutic effect. Generally, such doses will be in the range of about 1 mg/day to about 1000 mg/day; more preferably in the range of about 10 mg/day to about 500 mg/day. In another example embodiment, the compound or compounds may be present in a composition or formulation in a range of about 0.5 mg/kg/day to about 100 mg/kg/day or about 1 mg/kg/day to about 100 mg/kg/day. However, the actual amount of the compound to be administered in any given case will be determined by a physician taking into account the relevant circumstances, such as the age and weight of the patient, the patient's general physical condition, the severity of ocular condition, and the route of administration. In some instances, dosing is evaluated on a case-by-case basis.

In another example embodiment, provided are pharmaceutical compositions including at least one compound in a pharmaceutically acceptable carrier. Pharmaceutical compositions can be used in the form of a solid, a solution, an emulsion, a dispersion, a micelle, a liposome, and the like, wherein the resulting composition contains one or more compounds described herein, as an active ingredient, in admixture with an organic or inorganic carrier or excipient suitable for enteral or parenteral applications. One or more compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Compounds described herein are included in pharmaceutical compositions in an amount sufficient to produce the desired effect upon the process or disease condition.

In another embodiment, the compounds described herein can be administered orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, formulations may be designed to delay release of the active compound over a given period of time, or to carefully control the amount of drug released at a given time during the course of therapy.

Pharmaceutical compositions in a form suitable for oral use, for example, are administered as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing compounds described herein in admixture with non-toxic pharmaceutically acceptable excipients may also be manufactured by known methods.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug. The actual amount of the compound to be administered in any given case will be determined by a physician taking into account the relevant circumstances, such as the severity of the condition, the age and weight of the patient, the patient's general physical condition, the cause of the condition, and the route of administration. Described herein are compounds capable of modulating glucocorticoid receptors (GR) and/or mineralocorticoid receptors (MR). The compounds described can have greater GR activation and/or binding potency compared to a compound such as cortisol. As such, the compounds can efficiently treat ocular indications. The compounds can further be metabolized by esterase enzymes within the eye to form the natural agonist cortisol, thereby reducing the risk of ocular hypertension. The cortisol remaining within the eye and body is further metabolized to inactive compounds via naturally occurring dehydroxylases and other enzymes making this a safe therapeutic approach.

In patients, the naturally occurring endogenous GC agonist cortisol (hydrocortisone) has a minimal effect on intraocular pressure when applied locally via eye drops compared to synthetic GCs such as dexamethasone, prednisolone, and fluorometholone (Cantrill et al., 1975). Further support of the overall superior safety of cortisol as a therapeutic is the fact that various topical hydrocortisone formulations are currently sold over the counter directly to consumers.

Without wishing the bound to any particular theory, it was surprisingly discovered that the presently described compounds can have more glucocorticoid receptor modulation than cortisol because of the modification to the 17-position of the cortisol molecule.

As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the compounds are mixed with an inert solid diluent, for example, calcium carbonate, calcium phosphate or kaolin. They may also be in the form of soft gelatin capsules wherein the compounds are mixed with water or an oil medium, for example, peanut oil, liquid paraffin, or olive oil.

The compounds described herein can also be administered as an ophthalmically acceptable formulation or composition. A liquid which is ophthalmically acceptable is formulated such that it can be administered topically to the eye. The comfort should be maximized as much as possible, although sometimes formulation considerations (e.g. stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in ophthalmic compositions described herein include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations described herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In one example embodiment, an ophthalmic composition as described herein may have ingredients used in the following amounts listed in Table 1.

TABLE 1

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

In other embodiments, the ophthalmically acceptable liquid can be formulated for intraocular injection. The compounds described herein can be formulated as a liquid, gel paste, or the like for intraocular injection. Further, the compounds can be formulated into sustained release or controlled release intraocular implants comprising biodegradable polymers such as polylactic acid, poly glycolic acid, combinations thereof and the like.

Some exemplary compositions can include a combination of two or more compounds as described herein. Different ratios of compounds can be formulated depending on a particular ocular condition or set of conditions being treated.

Since individual subjects may present a wide variation in severity of symptoms and each composition has its unique therapeutic characteristics, the precise mode of administration and dosage employed for each subject is left to the discretion of the practitioner.

The present invention concerns also processes for preparing the compounds of Formula I. The compounds of Formula I according to the invention can be prepared analogously to conventional methods as understood by the person skilled in the art of synthetic organic chemistry. The synthetic scheme set forth below, illustrate how compounds according to the invention can be made.

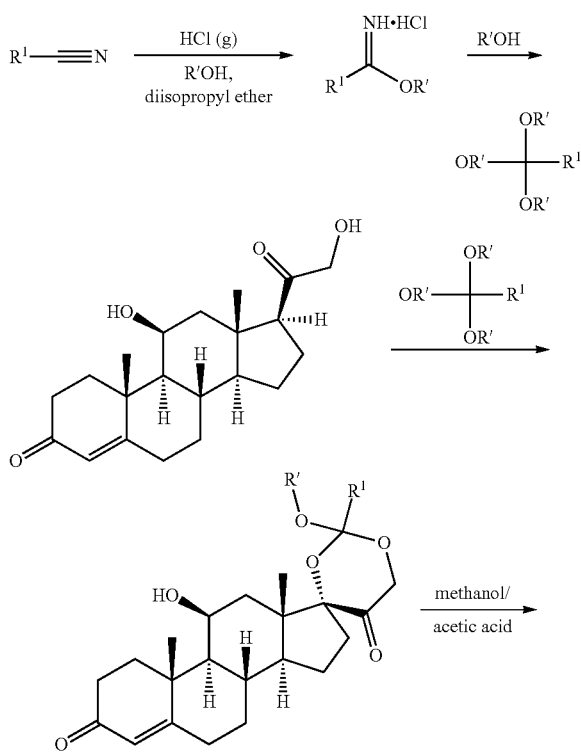

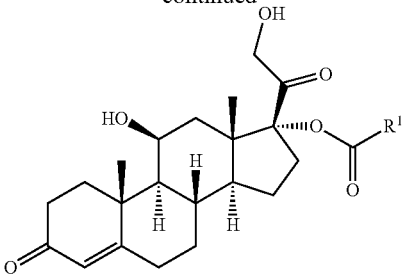

Formula I $R'$ is $C_1$-$C_4$ alkyl, or the like, preferably $CH_3$

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 12.0; and Intermediates and reagent names used in the examples were generated with software such as Chem Bio Draw Ultra version 12.0 or Auto Nom 2000 from MDL ISIS Draw 2.5 SP1.

In general, characterization of the compounds is performed according to the following methods:

NMR spectra are recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, AK Scientific, AmFine Com, Carbocore, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

Example 1

Intermediate 1

2-(Trimethoxymethyl)furan

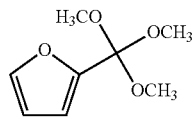

An anhydrous solution of HCl in methanol was prepared by slowly adding acetyl chloride (10.5 mL) to methanol (20 mL) at room temperature. The solution was stirred 2 h. After cooling in an ice bath under nitrogen, 2-furonitrile (12 mL, 137 mM) was added by syringe. The reaction was stirred in a dry atmosphere at 0° C. overnight. After warming to room temperature the intermediate was precipitated by the addition of dry ether (50 mL). It was filtered out in a dry sintered glass funnel in a dry box and washed with dry ether. After ether evaporation the solid was treated with dry methanol and stirred at 50° C. for 70 h. The mixture was treated with dry ether (60 mL) and ammonium chloride was removed by filtration through a dry sintered glass funnel. Concentration of the filtrate gave the title compound (6 g) as a colorless oil.

Example 2

Intermediate 2 rel-(8R,9R,10S,11R,13R,14R,17S)-2'-(2-furyl)-1'-hydroxy-2'-methoxy-10,13-dimethyl-1,6,7,8,9,10,11,12,13,14,15,16-dodecahydro-5'H-spiro[cyclopenta[a]phenanthrene-17,4'-[1,3]dioxane]-3,5'(2H)-dione

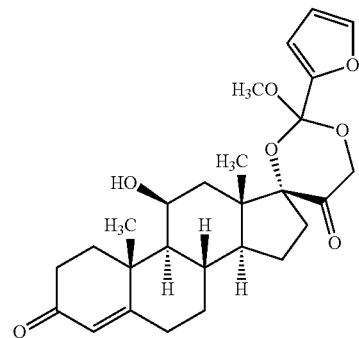

A solution of cortisol (10.4 g, approximately 28 mM), dried by evaporation from ethanol-butanol) in dry tetrahydrofuran (40 mL) was treated with crude Intermediate 1 (5.4 g, 32 mM) and 0.5 mL of a solution of anhydrous p-toluenesulfonic acid in toluene (approximately 0.7 M). The reaction was stirred at room temperature 48 h. Additional dry THF was added (100 mL) and anhydrous p-TSA solution (2 mL), and the reaction was stirred 48 h. The reaction was partially concentrated and stirred another night. The reaction was partitioned between ethyl acetate and aqueous dibasic sodium phosphate. The organic layer was washed with brine, dried, and evaporated. The residue was purified by chromatography (silica gel, 30-70 ethyl acetate-dichloromethane) and gave Intermediate 2 (0.9 g).

Example 3

Compound 1

(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl 2-furoate

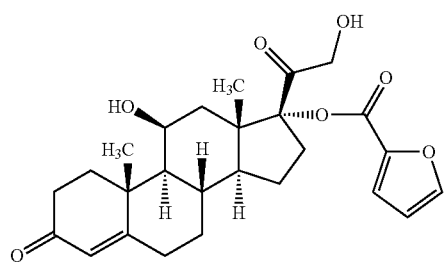

Intermediate 1 was dissolved in tetrahydrofuran (20 mL) and cooled in and ice/salt water bath under an inert atmosphere. The solution was treated with 0.37 mL of a 1M aqueous sulfuric acid solution. The reaction was stirred cold for 2 h. The reaction worked up with dibasic sodium phosphate solution and ethyl acetate. The ethyl acetate solution was washed with brined, dried and evaporated. The product was purified by chromatography (silica gel 60, 50-50 ethyl acetate-dichloromethane) and concentrated. The residue was crystallized from dichloromethane-hexane to give Compound 1 (1.9 g, 82%).

NMR (CDCl$_3$, TMS): δ 1.00 (s, 3H), 1.13 (m, 3H), 1.47 (s, 3H), 1.51 (m, 1H), 2.54-1.74 (m's, 13H), 2.90 (m, 1H), 3.08 (m, 1H), 4.37 (m, 2H), 4.56 (m, 1H), 5.71 (s, 1H), 6.54 (m, 1H), 7.20 (m, 1H), 7.61 (m, 1H).

Example 4

Intermediate 3

Methyl 2-(4-bromophenyl)acetimidate hydrochloride

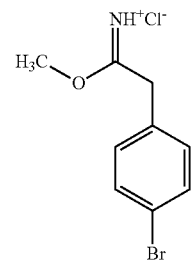

In a manner similar to that described in Example 1, 2-(4-bromophenyl)acetonitrile is converted to Intermediate 3. The residue that was obtained was not treated with methanol but isolated to give Intermediate 3.

Example 5

Intermediate 4 rel-(8R,9R,10S,11R,13R,14R,17S)-2'-(4-bromobenzyl)-11-hydroxy-2'-methoxy-10,13-dimethyl-1,6,7,8,9,10,11,12,13,14,15,16-dodecahydro-5'H-spiro[cyclopenta[a]phenanthrene-17,4'-[1,3]dioxane]-3,5'(2H)-dione

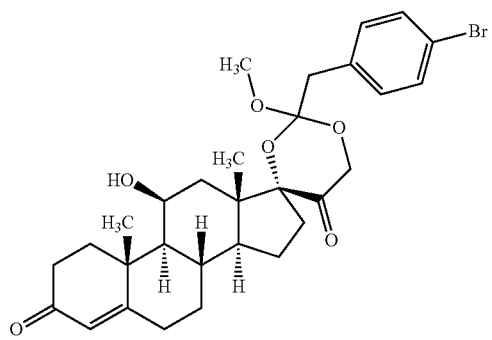

In a manner similar as described in Example 2, cortisol and Intermediate 3 were converted to Intermediate 4. Purification by silica gel flash chromatography (20% ethyl acetate in $CH_2Cl_2$ elution) provided the 24.8 mg of Intermediate 4: ICMS-ESI (m/z): calculated for, $C_{30}H_{37}BrO_6$, 572, 574; [M+H]$^+$ found 573, 575.

Example 6

Compound 2

(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl (4-bromophenyl)acetate

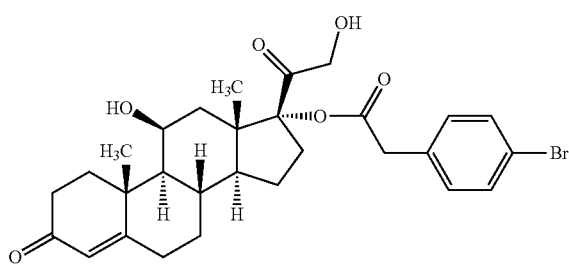

In a manner similar as described in Example 3, Intermediate 4 was converted to Compound 2. Purification of the crude reaction mixture by silica gel chromatography (20% ethyl acetate, methylene chloride) provided the 57.7 mg of Compound 2. ICMS-ESI (m/z): calculated for, $C_{29}H_{35}BrO_6$, 558, 560; [M+H]$^+$ found 559, 561.

Example 7

Intermediate 5 rel-(8R,9R,10S,11R,13R,14R,17S)-2'-ethoxy-11-hydroxy-10,13-dimethyl-2'-[2-(phenylsulfonyl)ethyl]-1,6,7,8,9,10,11,12,13,14,15,16-dodecahydro-5'H-spiro[cyclopenta[a]phenanthrene-17,4'[1,3]dioxane]-3,5'(2H)-dione

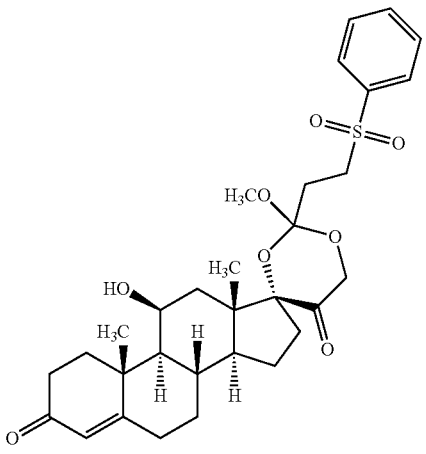

In a manner similar as described in Example 2, cortisol and ((3,3,3-trimethoxypropyl)sulfonyl)benzene were converted to Intermediate 5. Purification of the crude reaction mixture by silica gel chromatography (20% ethyl acetate, methylene chloride) provided the 13.1 mg of Intermediate 5. ICMS-ESI (m/z): calculated for, $C_{32}H_{42}O_8S$, 586; [M+H]$^+$ found 587.

Example 8

Compound 3

(8S,9S,10R,11S,13S,14S,17R)-17-glycoloyl-11-hydroxy-10,13-dimethyl-3-oxo-2,3,6,7,8,9,10,11,12,13,14,15,16,17-tetradecahydro-1H-cyclopenta[a]phenanthren-17-yl 3-(phenylsulfonyl)propanoate

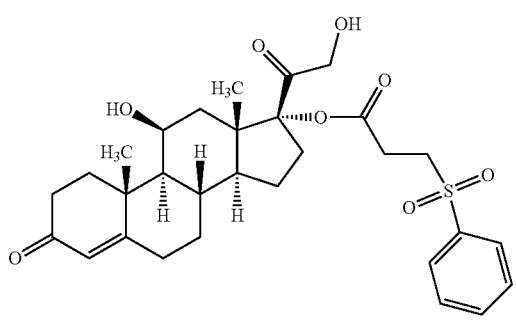

In a manner similar to experiment described in Example 3, Intermediate 5 was converted to the title compound. Purification of the crude reaction mixture by silica gel chromatography (20% ethyl acetate, methylene chloride) provided the 96.9 mg of Compound 3. ICMS-ESI (m/z): calculated for $C_{30}H_{38}O_6S$, 558; [M+H]$^+$ found 559.

Example 9

Glucocorticoid Receptor Transactivation Potencies for Cortisol and 17-Ester Derivatives Glucocorticoid receptor (GR) activation potency was assessed using a HeLa cell line containing the MMTV-bla reporter (MMTV-bla HeLa CELLSENSOR®, Invitrogen Corp., Carlsbad, Calif.). This cell line was stably transfected with an expression construct containing β-lactamase cDNA under control of the MMTV response element previously identified as a glucocorticoid receptor response element.

Results from one experiment performed in duplicate for the compounds and the control compound, dexamethasone, are summarized in Table 2. All assays were performed as 10-point dose responses using a half log-fold dilution series starting with a maximum compound concentration of 100 nM. The compounds were incubated for 5 hours. The activation of endogenous GR leads to expression of the reporter β-lactamase which is detected by the conversion of a FRET substrate in a ratiometric assay format. This functional assay allows for measurement of receptor agonism by compounds and can be used to determine compound potency and selectivity. Assay reproducibility was determined by calculating Z' values for untreated versus maximum stimulation. The Z' value was greater than 0.6, indicating good reproducibility of the assay format.

Several compounds showed dose-dependent stimulation of the GR signaling pathway (Table 2). Two compounds, cortisol 17-cyclopentanoate and cortisol 17-benzoate, showed about 30-fold greater potency compared to the parent molecule cortisol.

TABLE 2

Glucocorticoid receptor potency. Shown are the $EC_{50}$ (nM) and Z' values for the control compound, dexamethasone, and the compounds tested in agonist mode.

| Compound | EC50 (nM) GR | % Activation at 100 nM | Z' |
| --- | --- | --- | --- |
| Dexamethasone | 1.05 | Control Compound | 0.87 |
| Cortisol | 41.6 | 43 | 0.87 |
| Compound 3 | >100 | 17 | 0.87 |

TABLE 2-continued

Glucocorticoid receptor potency. Shown are the $EC_{50}$ (nM) and Z' values for the control compound, dexamethasone, and the compounds tested in agonist mode.

| Compound | EC50 (nM) GR | % Activation at 100 nM | Z' |
|---|---|---|---|
| Compound 2 | — | 0 | 0.87 |

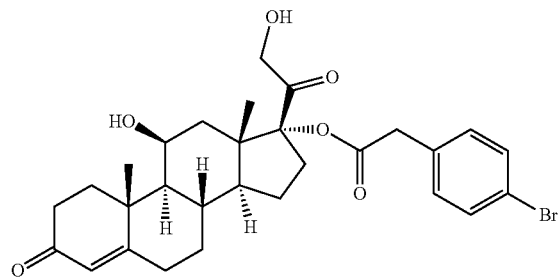

Example 10

Mineralocorticoid Receptor Transactivation Potencies for Cortisol and 17-Ester Derivatives Mineralocorticoid receptor (MR) activation potency was assessed using a HEK 293T cell line containing the UAS-bla reporter (UAS-bla HEK 293T CELLSENSOR®). This cell line was stably cotransfected with an expression construct containing β-lactamase cDNA under control of the GAL4 Upstream Activator Sequence (UAS) and another expression construct encoding for the fusion protein GAL4(DBD)-MR (LBD). Results for one experiment performed in duplicate for the novel compounds and the control compound, aldosterone, in agonist mode are summarized in Table 2. All assays were performed as 10-point dose responses using a half log-fold dilution series starting with a maximum compound concentration of 100 nM. The compounds were incubated for 16 hours. The activation of the fusion protein GAL4(DBD)-MR (LBD) leads to expression of the reporter β-lactamase which is detected by the conversion of a FRET substrate in a ratiometric assay format. This functional assay allows for measurement of receptor agonism by compounds and can be used to determine compound potency and selectivity. Assay reproducibility was determined by calculating Z' values for untreated versus maximum stimulation. The Z' value was greater than 0.6, indicating good reproducibility of the assay format. Several compounds showed dose-dependent stimulation of the MR signaling pathway (Table 3).

TABLE 2

Mineralocorticoid receptor potency. Shown are the $EC_{50}$ (nM) and Z' values for the control compound, aldosterone, and the compounds tested in agonist mode.

| Compound | EC50 (nM) GR | % Activation at 100 nM | Z' |
|---|---|---|---|
| Aldosterone | 0.47 | Control Compound | 0.77 |
| Cortisol | 2.90 | 75 | 0.77 |

TABLE 2-continued

Mineralocorticoid receptor potency. Shown are the $EC_{50}$ (nM) and Z' values
for the control compound, aldosterone, and the compounds tested in agonist mode.

| Compound | EC50 (nM) GR | % Activation at 100 nM | Z' |
|---|---|---|---|
| Compound 3 | 3.48 | 79 | 0.77 |
| Compound 2 | 5.53 | 77 | 0.77 |

Example 11

Treating Elevated Intraocular Pressure

A 58 year old male visits his ophthalmologist for a routine check-up. The physician discovers that the patient exhibits an elevated intraocular pressure and is at high risk for future complications. The patient is instructed to apply a topical liquid formulation containing one of the compounds in Table 1 once daily to each eye.

The patient returns for a follow-up visit three months later. Upon measuring intraocular pressure, it is noted that the patient now exhibits a reduced intraocular pressure.

Example 12

Treating Ocular Irritation

A 38 year old male visits his ophthalmologist complaining of irritation in his right eye. The physician discovers that the patient's right eye is inflamed and red. The patient is instructed to apply a topical liquid formulation containing one of the compounds in Table 1 twice daily to the right eye.

The patient returns for a follow-up visit a week later. Upon inspection of the right eye, it is noted that the patient's eye is no longer red and the patient indicates that the irritation is gone.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating a disorder associated with glucocorticoid receptor modulation, which comprises administering to a patient an ophthalmically acceptable pharmaceutical composition comprising a therapeutically effective amount of a compound, or a pharmaceutically acceptable salt thereof, wherein the compound is selected from the group consisting of:

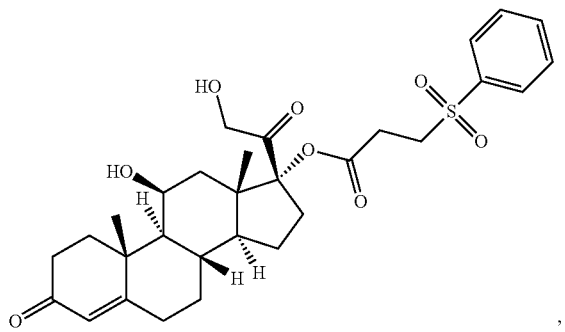

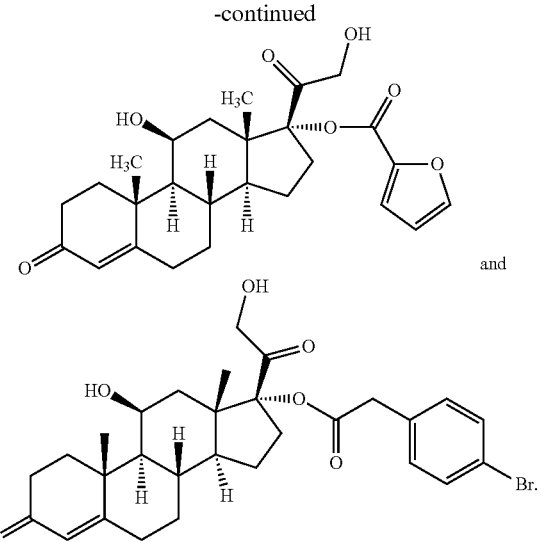

and

2. The method according to claim 1 wherein the disorder associated with glucocorticoid receptor modulation is selected from the group consisting of elevated intraocular pressure, glaucoma, retinal vein occlusions, diabetic retinopathy, various forms of macular edema, post-surgical inflammation, inflammatory conditions of the palpebral and bulbar conjunctiva, cornea, and anterior segment of the globe, retinal detachment, superficial punctate keratitis, herpes zoster keratitis, iritis, cyclitis, selected infective conjunctivitis, corneal injury from chemical, radiation, or thermal burns, penetration of foreign bodies, allergy, or combinations thereof.

3. The method according to claim 1 wherein the disorder associated with glucocorticoid receptor modulation is selected from dry eye, blepharitis, ocular rosacea, meibomian gland dysfunction, uveitis and macular degeneration.

4. The method according to claim 3 wherein the disorder associated with glucocorticoid receptor modulation is dry eye.

5. The method according to claim 1 wherein the ophthalmically acceptable pharmaceutical composition is topically administered.

6. The method according to claim 4 wherein the ophthalmically acceptable pharmaceutical composition is topically administered.

7. The method according to claim 1 wherein the ophthalmically acceptable pharmaceutical composition is formulated for intraocular injection.

8. The method according to claim 4 wherein the ophthalmically acceptable pharmaceutical composition is formulated for intraocular injection.

9. The method according to claim 1 wherein the ophthalmically acceptable pharmaceutical composition is formulated into sustained release or controlled release intraocular implants comprising biodegradable polymers.

10. The method according to claim 4 wherein the ophthalmically acceptable pharmaceutical composition is formulated into sustained release or controlled release intraocular implants comprising biodegradable polymers.

11. The method according to claim 9, wherein the biodegradable polymer is selected from the group consisting of polylactic acid, plyglycolic acid, and combinations thereof.

12. The method according to claim 10, wherein the biodegradable polymer is selected from the group consisting of polylactic acid, plyglycolic acid, and combinations thereof.

* * * * *

UNITED STATES PATENT AND TRADEMARK OFFICE
CERTIFICATE OF CORRECTION

PATENT NO. : 9,433,631 B2  
APPLICATION NO. : 14/533847  
DATED : September 6, 2016  
INVENTOR(S) : Jeffrey L. Edelman et al.

Page 1 of 1

It is certified that error appears in the above-identified patent and that said Letters Patent is hereby corrected as shown below:

On the Title Page

In item (56), in Column 2, under "Other Publications", Line 5, delete "Chemica" and insert -- Chimica --, therefor.

In the Specification

In Column 6, Line 9, delete "receptors (MR). receptors." and insert -- receptors (MR). --, therefor.

In Column 11, Line 43, delete "-1'-" and insert -- -11- --, therefor.

In Column 14, Line 8, delete "4'[1,3]" and insert -- 4'-[1,3] --, therefor.

In the Claims

In Column 22, Line 62, in Claim 11, delete "plyglycolic" and insert -- polyglycolic --, therefor.

In Column 22, Line 65, in Claim 12, delete "plyglycolic" and insert -- polyglycolic --, therefor.

Signed and Sealed this  
Fourteenth Day of February, 2017

Michelle K. Lee  
*Director of the United States Patent and Trademark Office*